United States Patent [19]
Garthoff et al.

[11] Patent Number: 4,703,038
[45] Date of Patent: Oct. 27, 1987

[54] COMBINATION OF DIHYDROPYRIDINES WITH ANGIOTENSIN CONVERTING ENZYMES-INHIBITORS

[75] Inventors: Bernward Garthoff, Hilden; Stanislav Kazda; Andreas Knorr, both of Wuppertal, all of Fed. Rep. of Germany

[73] Assignee: Bayer Aktiengesellschaft, Leverkusen, Fed. Rep. of Germany

[21] Appl. No.: 785,182

[22] Filed: Oct. 7, 1985

[30] Foreign Application Priority Data

Oct. 17, 1984 [DE] Fed. Rep. of Germany ....... 3437917

[51] Int. Cl.⁴ .................. A61K 31/455; A61K 31/44; A61K 37/02; C07C 103/52
[52] U.S. Cl. ..................................... 514/19; 514/302; 514/356
[58] Field of Search ............................... 530/331, 316; 260/998.2; 514/19, 302, 356, 929

[56] References Cited

U.S. PATENT DOCUMENTS

| | | | |
|---|---|---|---|
| 3,966,946 | 6/1976 | Roe et al. | 514/356 |
| 3,966,948 | 6/1976 | Bossert et al. | 514/302 |
| 3,971,791 | 7/1976 | Meyer et al. | 546/159 |

FOREIGN PATENT DOCUMENTS 0012401 6/1980 European Pat. Off. .

Primary Examiner—John Kight
Assistant Examiner—Nathan M. Nutter
Attorney, Agent, or Firm—Sprung Horn Kramer & Woods

[57] ABSTRACT

The invention concerns a combination of dihydropyridine derivatives with compounds which inhibit the formation of enzymes which control the conversion of angiotensin I into angiotensin II and their use as antihypertensive agents.

17 Claims, No Drawings

COMBINATION OF DIHYDROPYRIDINES WITH ANGIOTENSIN CONVERTING ENZYMES-INHIBITORS

The present invention relates to a combination of dihydropyridine compounds with compounds which inhibit the formation of enzymes which control the conversion of angiotensin I into angiotensin II, and its use in medicaments, in particular in antihypertensive medicaments.

Compounds which inhibit the formation of enzymes which convert angiotensin I into angiotensin II are called ACE inhibitors (angiotensin converting enzymes). These compounds are known as antihypertensive agents, since they reduce the blood pressure if the hypertension can be attributed to angiotensin II.

When used therapeutically, ACE-inhibiting compounds must be used in relatively high dosages in a large number of hypertensive patients, which can lead to deterioration of the patients due to side effects.

ACE-inhibiting compounds which may be mentioned are those of the following formula (I)

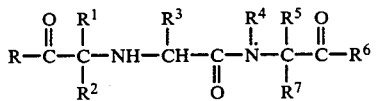

wherein
R and $R^6$ are identical or different and are hydroxyl, lower alkoxy, lower alkenoxy, di-lower alkylamino-lower alkoxy, acylamino-lower alkoxy, acyloxy-lower alkoxy, aryloxy, Ar-lower alkoxy, substituted aryloxy or substituted Ar-lower alkoxy, the substituent being methyl, halogen or methoxy, amino, lower alkylamino, di-lower alkylamino, aryl-lower alkylamino or hydroxylamino, $R^1$ denotes hydrogen, alkyl with 1 to 20 carbon atoms, which includes branched cyclic and unsaturated alkyl groups, substituted lower alkyl, the substituent being halogen, hydroxyl, lower alkoxy, aryloxy, amino, lower alkylamino, di-lower alkylamino, acylamino, arylamino, guanidino, imidazolyl, indolyl, mercapto, lower alkylthio, arylthio, carboxyl, carboxamido or carbo-lower alkoxy, phenyl, substituted phenyl, the substituent being lower alkyl, lower alkoxy or halogen, Ar-lower alkyl or heteroar-lower alkyl, Ar-lower alkenyl or heteroan-lower alkenyl, substituted Ar-lower alkyl, substituted heteroar-lower alkyl, substituted Ar-lower alkenyl or substituted heteroar-lower alkenyl, the substituent being halogen or dihalogen, lower alkyl, hydroxyl, lower alkoxy, amino, aminomethyl, acylamino, di-lower alkylamino, lower alkylamino, carboxyl, halogeno-lower alkyl, cyano or sulphonamido; or Ar-lower alkyl or heteroar-lower alkyl, which is substituted on the alkyl part by amino or acylamino, $R^2$ and $R^7$ denote hydrogen or lower alkyl, $R^3$ is hydrogen, lower alkyl, phenyl-lower alkyl, aminomethylphenyl-lower alkyl, hydroxyphenyl-lower alkyl, hydroxy-lower alkyl, acylamino-lower alkyl, amino-lower alkyl, dimethylamino-lower alkyl, halogen-lower alkyl, guanidino-lower alkyl, imidazolyl-lower alkyl, indolyl-lower alkyl, mercapto-lower alkyl or lower alkylthio-lower alkyl, $R^4$ is hydrogen or lower alkyl and $R^5$ is hydrogen, lower alkyl, phenyl, pheny-lower alkyl, hydroxyphenyl-lower alkyl, hydroxy-lower alkyl, amino-lower alkyl, guanidino-lower alkyl, imidazolyl-lower alkyl, indolyl-lower alkyl, mercapto-lower alkyl or lower alkylthio-lower alkyl, or $R^4$ and $R^5$ can be linked to one another to form an alkylene bridge with 2 to 4 carbon atoms, an alkylene bridge with 2.or 3 carbon atoms and one sulphur atom or an alkylene bridge which has 3 or 4 carbon atoms and contains a double bond or an alkylene bridge as above, substituted by hydroxyl, lower alkoxy, lower alkyl or di-lower alkyl, and the pharmaceutically acceptable salts thereof.

Preferred compounds which may be mentioned are those of the formula (I)

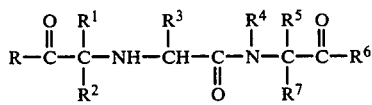

wherein
R is hydroxyl, lower alkoxy, lower alkenoxy, Ar-lower alkoxy, di-lower alkylamino-lower alkoxy, acylamino-lower alkoxy or acyloxy-lower alkoxy, $R^6$ is hydroxyl or amino, $R^1$ represents alkyl with 1 to 8 carbon atoms, substituted lower alkyl, the alkyl group having 1 to 4 carbon atoms and the substituent being amino, arylthio, aryloxy or arylamino, aralkyl or heteroaralkyl, the alkyl section having 1 to 3 carbon atoms; or substituted aralkyl or heteroaralkyl, the alkyl groups having 1 to 3 carbon atoms and the substituent or substituents being halogen, dihalogen, amino, aminoalkyl, hydroxyl, lower alkoxy or lower alkyl, $R^2$ and $R^7$ are hydrogen, $R^3$ is lower alkyl or amino-lower alkyl and $R^4$ and $R^5$ can be linked together, via the carbon and nitrogen atoms to which they are bonded, to form a ring of the formula

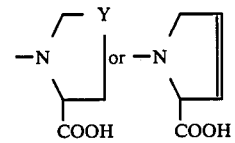

wherein
Y, is $CH_2$, S or $CHOCH_3$,
and the pharmaceutically acceptable salts thereof.

Particularly preferred compounds which may be mentioned are those of the formula (I)

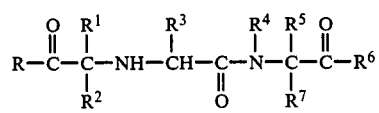

wherein
R is hydroxyl or lower alkoxy,
$R^6$ is hydroxyl, $R^2$ and $R^7$ are hydrogen, $R^3$ is methyl or amino-lower alkyl, $R^4$ and $R^5$ are linked via the carbon and nitrogen atom to form proline, 4-thiaproline or 4-methoxy proline and $R^1$ denotes alkyl with 1 to 8 carbon atoms, substituted lower alkyl, the alkyl group having 1 to 4 carbon atoms and the substituent being amino, arylthio or aryloxy, aralkyl or heteroaralkyl, the alkyl section having 1 to 3 carbon atoms, or substituted aralkyl or substituted heteroaralkyl, the alkyl groups having 1 to 3 carbon atoms and the substituent or substituents being halogen, dihalogen, amino, aminoalkyl, hydroxyl, lower alkoxy or lower alkyl, and the pharmaceutically acceptable salts thereof.

The term "lower" preferably characterises 1 to 4 C atoms, with the exception of the amino-lower alkyl radical in the radical $R^3$, in which it denotes 1 to 6 C atoms. "Acyl" contains, in particular, 1 to 4 C atoms and aryl or Ar contains 6 or 10 C atoms.

Compounds which may be mentioned in particular are: N-(1-(S)-ethoxycarbonyl-3-phenylpropyl)-L-alanyl-L-proline L-proline or the maleate salt thereof (generic: enalapril) and N-(1-(S)-carboxy-3-phenylpropyl)-L-lysyl-L-proline (generic: lisinopril).

The preparation of these compounds is described in European Offenlegungsschrift (European Published Specification) 12,401.

Dihydropyridines are known as antihypertensive compounds, this action occurring by inhibition of the flow of calcium into the smooth muscle cells of the blood vessel.

Preferred dihydropyridines are those compounds of the formula (II)

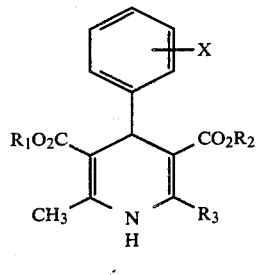

(II)

in which $R_1$ denotes $C_1$-$C_4$-alkyl, optionally substituted by $C_1$-$C_3$-alkoxy, $R_2$ denotes $C_1$-$C_{10}$-alkyl, optionally substituted by $C_1$-$C_3$-alkoxy, trifluoromethyl, trifluoroethyl or N-methyl-N-benzylamino, $R_3$ denotes $C_1$-$C_4$-alkyl, cyano or hydroxy-methyl and X denotes 2- or 3-nitro, 2-chloro, 2,3-dichloro or a 2,3-ring member consisting of =N-O-N=.

The compounds of the following table are particularly preferred:

TABLE

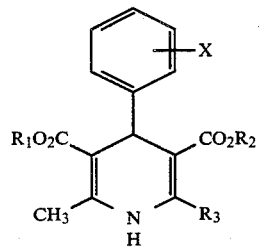

| No. | X | $R^1$ | $R^2$ | $R^3$ | Generic |
|---|---|---|---|---|---|
| 1 | 2-$NO_2$ | $CH_3$ | $CH_3$ | $CH_3$ | Nifedipine |
| 2 | 3-$NO_2$ | nPrOCH$_2$CH$_2$ | nPrOCH$_2$CH$_2$ | $CH_3$ | Niludipine |
| 3 | 3-$NO_2$ | $C_2H_5$ | $CH_3$ | $CH_3$ | Nitrendipine |
| 4 | 2-$NO_2$ | $CH_3$ | $(CH_3)_2CHCH_2$ | $CH_3$ | Nisoldipine |
| 5 | 3-$NO_2$ | $CH(CH_3)_2$ | $(CH_2)_2$—O—$CH_3$ | $CH_3$ | Nimodipine |
| 6 | 3-$NO_2$ | $C_2H_5$ | $C_{10}H_{21}$(n) | $CH_3$ | |
| 7 | 2-Cl | $CH_3$ | $CH_2$—$CF_3$ | $CH_3$ | |
| 8 | 2-Cl | $C_2H_5$ | $CH_2$—$CF_3$ | $CH_3$ | |
| 9 | 3-$NO_2$ | $CH(CH_3)_2$ | n-PrO—$CH_2CH_2$ | $CH_3$ | |
| 10 | 3-$NO_2$ | $CH_3$ | $C_6H_5CH_2N(CH_3)CH_2CH_2$ | $CH_3$ | Nicardipine |
| 11 | 2,3-$Cl_2$ | $C_2H_5$ | $CH_3$ | $CH_3$ | Felodipine |
| 12 | 2,3=N—O—N= | $C_2H_5$ | $C_2H_5$ | $CH_3$ | |
| 13 | 2,3=N—O—N= | $CH_3$ | $CH(CH_3)_2$ | $CH_3$ | |
| 14 | 3-$NO_2$ | $C_2H_5$ | $C_2H_5$ | $CH_2OH$ | |
| 15 | 3-$NO_2$ | $CH(CH_3)_2$ | $CH_3$ | CN | | n-Pr = n-propyl

Compounds which may be mentioned in particular are: nitrendipine, nisoldipine, nicardipine and felodipine.

The present invention is based on the finding that, by combination with dihydropyridines, a surprising intensification of the action of the ACE inhibitors occurs and thus it is possible to reduce the dose.

1-10 parts by weight, preferably 1-3 parts by weight a in particular 3 parts by weight, of the dihydropyridine can be employed per part by weight of an ACE inhibitor.

The combination can be prepared by dissolving the individual components in inert solvents which dissolve these and, after evaporating off the solvent, mixing the combination with auxiliaries in the customary manner.

Examples of inert solvents which may be mentioned are alcohols, such as ethanol, or glycols, such as polyethylene glycol.

As already mentioned, the combination according to the invention can be used to combat diseases, in particular circulatory diseases, in particular for the treatment of hypertension, cardiac insufficiency and/or coronary heart disease.

The active compound combination can be converted in a known manner into the customary formulations, such as tablets, capsules, dragees, pills, granules, aerosols, syrups, emulsions, suspensions and solutions, using inert, non-toxic pharmaceutically suitable excipients or solvents. The combination of the therapeutically active compounds should in each case be present here in a concentration of about 0.5 to 50% by weight of the total mixture, that is to say in amounts which are sufficient to achieve the abovementioned dosage range.

These formulations are prepared, for example, by extending the active compounds with solvents and/or excipients, optionally with the use of emulsifying agents and/or dispersing agents, and, for example when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silica and silicates) and sugars (for example sucrose, lactose and glucose), emulsifying agents (for example polyoxyethylene fatty acid esters, polyoxyethylene fatty alcohol ethers, alkylsulpnonates and arylsulphonates), dispersing agents (for example lignin, sulphite waste liquors, methylcellulose, starch and polyvinylpyrrolidone) and lubricants (for example magnesium stearate, talc, stearic acid and sodium laurylsulphate).

Administration is effected in the customary manner, preferably orally or parenterally, and in particular perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatin and the like. Furthermore, lubricants, such as magnesium stearate, sodium lauryl sulphate and talc, can be co-used when making tablets. In the case of aqueous suspensions and/or elixirs which are intended for oral use, the active compounds can be mixed with various flavour-improving agents or colorants in addition to the abovementioned auxiliaries.

In the case of parenteral use, solutions of the active compounds can be employed, using suitable liquid excipients.

The antihypertensive activity of the combination according to the invention may be demonstrated using the example of the combination of enalapril and nitrendipine:

The activity following oral administration was determined on conscious rats in which hypertension had been produced by ligation of the main artery between the two renal arteries. The special test arrangement according to Garthoff and Towart (J. Pharmacol Methods 5, 275–278, 1981) was used to record the blood pressure over 24 hours.

Oral administration of nitrendipine leads to a reduction in blood pressure which is dose-dependent but is of only limited duration. Although enalapril causes a lasting reduction in blood pressure in these rats, the action can be substantially increased by simultaneous administration of a small dose of nitrendipine (see table). On the other hand, administration of enalapril in addition to nitrendipine increases the reduction in blood pressure to over 9 hours after the administration. This means that, with an improved and extended action, the individual components can be reduced or the individual doses can be halved (see table).

It is thus advantageous for the dosages customary for humans (that is to say 2.5–40 mg of enalapril/day or 10–60 mg of nitrendipine/day) to be limited in the combination. Preferably, on oral administration, the two substances are administered in a combination of 2.5–15 mg (enalapril) and 10–20 mg (nitrendipine) per day.

Nevertheless, it can at times be necessary to deviate from the amounts mentioned, and in particular to do so as a function of the body weight or of the nature of the administration route, but also because of the individual behavior towards the combination or the nature of the formulation and the time or interval over which administration takes place. Thus it can suffice in some cases to manage with less than the abovementioned minimum amount, whilst in other cases the limit mentioned must be exceeded. Where relatively large amounts are administered, it may be advisable to divide these up into several individual administrations over the course of the day.

TABLE 1

Blood pressure values (systolic upper half, diastolic lower half) in mm Hg before and after oral administration of the angiotensin converting enzyme inhibitor enalapril or the calcium antagonist nitrendipine and the combination of the two substances.

| | | Minutes after administration | | | | | Hours after administration | | | |
|---|---|---|---|---|---|---|---|---|---|---|
| | n | 0 | 12 | 24 | 36 | 48 | 60 | 2 h | 4 h | 6 h | 9 h |
| Enalapril, 1 mg/kg p.o. | 10 | 198 ± 6 | 195 ± 6 | 170 ± 7 | 165 ± 8 | 164 ± 5 | 158 ± 4 | 167 ± 7 | 173 ± 9 | 175 ± 8 | 194 ± 11 |
| Nitrendipine 3.15 mg/kg p.o. | 6 | 212 ± 8 | 146 ± 14 | 144 ± 8 | 138 ± 7 | 142 ± 7 | 146 ± 6 | 174 ± 8 | 201 ± 9 | 208 ± 10 | 227 ± 7 |
| Combination of enalapril (1 mg/kg p.o.) and nitrendipine (3.15 mg/kg p.o.) | 10 | 202 ± 3 | 163 ± 6 | 138 ± 6 | 132 ± 4 | 134 ± 5 | 138 ± 5 | 152 ± 5 | 168 ± 4 | 175 ± 4 | 185 ± 8 |
| Combination of enalapril (0.5 mg/kg p.o.) and nitrendipine (1.6 mg/kg p.o.) | 9 | 221 ± 8 | 162 ± 9 | 142 ± 9 | 146 ± 10 | 149 ± 11 | 150 ± 10 | 165 ± 4 | 180 ± 7 | 184 ± 4 | 192 ± 12 |

TABLE 1-continued

Blood pressure values (systolic upper half, diastolic lower half) in mm Hg before and after oral administration of the angiotensin converting enzyme inhibitor enalapril or the calcium antagonist nitrendipine and the combination of the two substances.

| | | Minutes after administration | | | | | Hours after administration | | | |
|---|---|---|---|---|---|---|---|---|---|---|
| | n | 0 | 12 | 24 | 36 | 48 | 60 | 2 h | 4 h | 6 h | 9 h |
| Enalapril 1 mg/kg p.o. | 10 | 133 ± 3 | 133 ± 3 | 118 ± 6 | 111 ± 6 | 113 ± 5 | 105 ± 5 | 111 ± 7 | 112 ± 6 | 111 ± 6 | 121 ± 6 |
| Nitrendipine 3.15 mg/kg p.o. | 6 | 142 ± 2 | 110 ± 7 | 87 ± 6 | 88 ± 5 | 92 ± 4 | 97 ± 5 | 118 ± 6 | 134 ± 6 | 137 ± 4 | 146 ± 4 |
| Combination of enalapril (1 mg/kg p.o.) and nitrendipine (3.15 mg/kg p.o.) | 10 | 141 ± 3 | 121 ± 4 | 95 ± 5 | 87 ± 3 | 92 ± 4 | 94 ± 5 | 104 ± 5 | 117 ± 7 | 116 ± 7 | 123 ± 5 |
| Combination of enalapril (0.5 mg/kg p.o.) and nitrendipine (1.6 mg/kg p.o.) | 9 | 138 ± 7 | 107 ± 4 | 89 ± 4 | 92 ± 4 | 92 ± 4 | 95 ± 4 | 108 ± 5 | 115 ± 7 | 118 ± 7 | 120 ± 10 | n = number of experiments, the mean values and scatter (SEM) are stated

What is claimed is:

1. A combination of compounds comprising a compound of the formula I

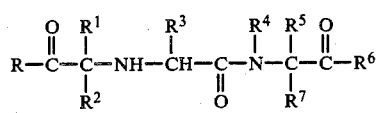

(I)

wherein

R and $R^6$ are independently hydroxyl, $C_1$-$C_4$-alkoxy, $C_2$-$C_4$-alkenoxy, di-$C_1$-$C_4$-alkylamino- $C_1$-$C_4$-alkoxy, acylamino-$C_1$-$C_4$-alkoxy, acylamino-$C_1$-$C_4$ alkoxy, acyloxy-$C_1$-$C_4$-alkoxy, aryloxy, Ar-$C_1$-$C_4$-alkoxy, substituted aryloxy or substituted Ar-$C_1$-$C_4$-alkoxy, the substituent being methyl, halogen or methoxy, amino, $C_1$-$C_4$-alkylamino, di-$C_1$-$C_4$- alkylamino, aryl-$C_1$-$C_4$-alkylamino or hydroxylamino, $R^1$ denotes hydrogen, alkyl with 1 to 20 carbon atoms, which includes branched cyclic and unsaturated alkyl groups, substituted $C_1$-$C_4$ alkyl, the substituent being halogen, hydroxyl, $C_1$-$C_4$-alkoxy, aryloxy, amino, $C_1$-$C_4$alkylamino, di-$C_1$-$C_4$-alkylamino, acylamino, arylamino, guanidino, imidazolyl, indolyl, mercapto, $C_1$-$C_4$-alkylthio, arylthio, carboxyl, carboxamido or carbo-$C_1$-$C_4$-alkoxy, phenyl, substituted phenyl, the substituent being $C_1$-$C_4$- alkyl, $C_1$-$C_4$-alkoxy or halogen, Ar-$C_1$-$C_4$-alkyl or heteroar-$C_1$-$C_4$- alkyl, Ar-$C_2$-$C_4$-alkenyl or heteroar-$C_2$-$C_4$alkenyl, substituted Ar-$C_1$-$C_4$-alkyl, substituted heteroar- $C_1$-$C_4$-alkyl, substituted Ar-$C_2$-$C_4$-alkenyl or substituted heteroar-$C_2$-$C_4$- alkneyl, the substituent being halogen or dihalogen, $C_1$-$C_4$-alkyl, hydroxyl, $C_1$-$C_4$- alkoxy, amino aminomethyl, acylamino, di-$C_1$-$C_4$-alkylamino, carboxyl, halogeno-$C_1$-$C_4$-alkyl, cyano or sulphoamido; or Ar-$C_1$-$C_4$ -alkyl or heteroar $C_1$-$C_4$- alkyl, which is substituted on the alkyl part by amino or acylamino, $R_2$ and $R_7$ denote hydrogen or $C_1$-$C_4$-alkyl, $R_3$ is hydrogen, $C_1$-$C_4$-alkyl, phenyl-$C_1$-$C_4$- alkyl, aminomethylphenyl- $C_1$-$C_4$-alkyl, hydroxyphenyl-$C_1$-$C_4$-alkyl, hydroxy-$C_1$-$C_4$- alkyl, acylamino-$C_1$-$C_4$-alkyl, amino-$C_1$-$C_6$-alkyl, dimethylamino-$C_1$-$C_6$alkyl, halogen-lower alkyl, guanidino-$C_1$-$C_4$-alkylm imidazolyl-$C_1$-$C_4$-alkyl, indolyl-$C_1$-$C_4$-alkyl, mercapto-$C_1$-$C_4$-alkyl or $C_1$-$C_4$-alkylthio-$C_1$-$C_4$-alkyl, $R^4$ is hydrogen or $C_1$-$C_4$- alkyl and $R^5$ is hydrogen, $C_1$-$C_4$-alkyl, phenyl, phenyl-$C_1$-$C_4$-alkyl, hydroxyphenyl-$C_1$-$C_4$alkyl, hydroxy-$C_1$-$C_4$-alkyl, amino-$C_1$-$C_4$-alkyl, amino-$C_1$-$C_4$-alkyl, guanidino-$C_1$-$C_4$- alkyl, imdazolyl-$C_1$-$C_4$- alkyl, indolyl- alkyl, mercapto, $C_1$-$C_4$-alkyl or $C_1$-$C_4$-alklyl or $C_1$-$C_4$-alkylthio-$C_1$-$C_4$-alkyl, or $R^4$ and $R^5$ can be linked to one another to form an alkylene bridge with 2 to 4 carbon atoms, an alkylene bridge with 2 or 3 carbon atoms and one sulphur atom or an alkylene bridge which has 3 or 4 carbon atoms and contains a double bond or an alkylene bridge as above, substituted by hydroxyl, $C_1$-$C_4$-alkoxy, $C_1$-$C_4$-alkyl or di-$C_1$-$C_4$-alkyl, and the pharmaceutically acceptable salts thereof, with a dihyropyridine compound of the formula II

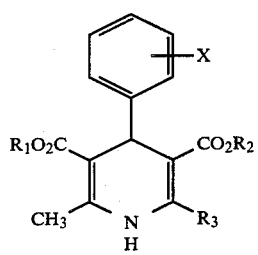

(II)

in which $R^1$ denotes $C_1$-$C_4$-alkyl, optionally substituted by $C_1$-$C_3$-alkoxy, $R^2$ denotes $C_1$-$C_{10}$-alkyl, optionally substituted by $C_1$-$C_3$-alkoxy, trifluoromethyl, trifluoroethyl or N-methyl-N-benzylamino, $R_3$ denotes $C_1$-$C_4$-alkyl, cyano or hydroxymethyl and X denotes 2- or 3-nitro, 2-chloro, 2,3-dichloro or a 2,3-ring member consisting of =N-O-N=.

2. A combination according to claim 1, wherein the definitions of the formula I have the following meanings:

R denotes hydroxyl, $C_1$-$C_4$-alkoxy, $C_2$-$C_4$-alkenoxy, Ar-$C_1$-$C_4$-alkyloxy, di-$C_1$-$C_4$-alkylamino-$C_1$-$C_4$-alkoxy, acylamino-$C_1$-$C_4$-alkoxy or acyloxy-$C_1$-$C_4$-alkoxy, R[6] denotes alkyl with 1 to 8 carbon atoms, substituted $C_1$-$C_4$ alkyl, the substituent being amino, arylthio, aryloxy or arylamino, aralkyl or heteroaralkyl, the alkyl section having 1 to 3 carbon atoms; or substituted aralkyl or heteroaralkyl, the alkyl groups having 1 to 3 carbon atoms and the substituent or substituents being halogen, dihalogen, amino, aminoalkyl, hydroxyl, $C_1$-$C_4$-alkoxy or $C_1$-$C_4$-alkyl, $R^2$ and $R^7$ hydrogen, $R^3$ $C_1$-$C_6$ -alkyl or amino-$C_1$-$C_6$-alkyl and $R^4$ and $R^5$ can be linked together, via the carbon and nitrogen atoms to which they are bonded, to form a ring of the formula

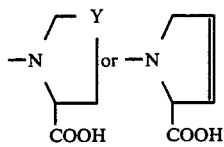

wherein

Y, is $CH_2$, S or $CHOCH_3$, and the pharmaceutically acceptable salts thereof.

3. A combination according to claim 1, wherein the definitions of the formula I have the following meanings:

R denotes hydroxyl or $C_1$-$C_4$- alkoxy $R^6$ denotes hydroxyl, $R^2$ and $R^7$ denote hydrogen, $R^3$ and $R^7$ denote hydrogen, $R^3$ denotes methyl or amino- $C_1$-$C_6$-alkyl, $R^4$ and $R^5$ Are linked via the carbon and nitrogen atom to form proline, 4-thiaproline or 4-methoxyproline and $R^1$ denotes alkyl with 1 to 8 carbon atoms, substituted $C_1$-$C_4$-alkyl, the substituent being amino, arylthio or aryloxy, arylkyl or heteroaralkyl, the alkyl section having 1 to 3 carbon atoms, or substituted aralkyl or substituted heteroaralkyl, the alkyl groups having 1 to 3 carbon atoms and the substituent or substituents being halogen, dihalogen, amino, aminoalkyl, hydroxyl, $C_1$-$C_4$-alkoxy or $C_1$-$C_4$-alkyl, and the pharmaceutically acceptable salts thereof.

4. A combination according to claim 1, wherein the compound formula I is selected from the group consisting of N-(1-(S)-ethoxycarbonyl-3-phenylpropyl)-L-alanyl-L-proline or its maleate salt and N-α-(1-(S -carboxy-3-phenylpropyl)-L-Lysyl-L-proline.

5. A combination according to claim 1, wherein the definition of the formula II have the following meanings:

X denotes 2-nitro, 3-nitro, 2-chloro, 2,3-dichloro or 2,3=N-O-N=, $R_1$ denotes methyl, ethyl, propyl or propyloxyethyl, $R_2$ denotes methyl, ethyl propyl, butyl and propyloxyethyl, methoxyethyl, decyl, trifluoromethylmethyl or 2-(N-benzyl-N-methyl)aminoethyl and $R_3$ denotes methyl, hydroxymethyl or cyano.

6. A combination according to claim 1, wherein the compound according to formula II is selected from the group consisting of nisoldipine, nicardipine and felodipine.

7. A combination according to claim 1, containing 1 part by weight of a compound according to formula I and 1–10 parts by weight of a dihydropyridine of the formula II.

8. A combination according to claim 1, containing 1 part by weight of a compound according to formula I and 1-3 parts by weight of a dihydropyridine of the formula II.

9. A combination according to claim 1, containing 1 part by weight of a compound according to formula I and 3 parts by weight of a dihydropyridine of the formula II.

10. A process for treating circulatory diseases by administering an effective amount of the combination of claim 1.

11. A process for treating hypertension by administering an effective amount of the combination of claim 1.

12. A medicament containing a combination according to claim 1.

13. A process for the preparation of the medicament, wherein the compounds according to formulae I and II of claim 1 are dissolved in inert solvents and, after the solvent has been evaporated off, the resulting combination is mixed, if appropriate with auxiliaries.

14. A combination of compounds comprising a mixture of a compound selected from the group consisting of N-(1-(S)pethoxycarbonyl-3-phenylpropyl)-L-alanyl-L-proline and its maleate salt and N-α-(1-(s) - carboxy-3-phenylpropyl)-L-Lysyl-L-proline and a dihydropyridine compound selected from the group consisting of nitrendipine, nisoldipine, nicardipine and felodipine.

15. A combination of compounds comprising a mixture of N-(1-(S)-ethyoxycarbonyl-3-phenylpropyl)-L-alanyl-proline and nitrendipine.

16. A process for treating hypertension by administering an effective amount of the combination of a compound selected from the group consisting of N-(1-(S)-ethoxycarbonyl-3-phenylpropyl)-L-alanyl-L-proline or it maleate salt and N-α-(1-(S)-carboxy-3-phenylpropyl)-L-Lysyl-L-proline dihydropyridine compound selected from the group consisting of nitrendipine, nisoldipine, nicardipine, and felodipine.

17. A process for treating hypertension by administering an effective amount of the combination of N-(1-(S)-ethoxycarbonyl-3-phenylpropyl)-L-alanyl-L-proline and nitrendipine.

* * * * *

UNITED STATES PATENT AND TRADEMARK OFFICE
CERTIFICATE OF CORRECTION

PATENT NO. : 4,703,038
DATED : Oct. 27, 1987
INVENTOR(S) : Garthoff et al.

It is certified that error appears in the above-identified patent and that said Letters Patent is hereby corrected as shown below:

| | |
|---|---|
| Col. 1, line 51 | Correct spelling of --heteroar-- |
| Col. 4, line 62 | Delete "a" and substitute --and-- |
| Col. 7, line 45 | Insert -- - -- after "$C_4$" in the first instance |
| Col. 7, line 52 | Insert -- - -- after "$C_4$" |
| Col. 7, line 55 | Correct spelling of --alkenyl-- |
| Col. 7, line 57 | Insert --,-- after "amino" |
| Col. 7, line 58 | Insert --$C_1$-$C_4$-alkylamino,-- after "alkylamino" |
| Col. 7, line 67 | Insert -- - -- after "$C_6$" |
| Col. 7, line 68 | Correct spelling of --alkyl-- in first instance and add --,-- after such correction |
| Col. 8, line 27 | Insert -- - -- after "$C_4$" in first instance |
| Col. 9, line 33 | Correct spelling of --are-- |
| Col. 9, line 49 | Delete "or" and substitute --and-- |
| Col. 10, line 47 | Delete "or" and substitute --and-- |
| Col. 10, line 49 | Insert --and a-- after "proline" |

Signed and Sealed this

Seventeenth Day of May, 1988

Attest:

Attesting Officer

DONALD J. QUIGG

Commissioner of Patents and Trademarks